(12) United States Patent
Hundertmark et al.

(10) Patent No.: US 9,579,441 B2
(45) Date of Patent: Feb. 28, 2017

(54) FILLING DEVICE OF A FLUID SYSTEM

(71) Applicant: B. BRAUN AVITUM AG, Melsungen (DE)

(72) Inventors: Charleen Hundertmark, Kassel (DE); Judith Hieronymi, Gudensberg (DE); Michele Susca, Dossenheim (DE); Anne-Marie Mihailescu, Melsungen (DE); Claudia Freitag, Gudensberg (DE); Rainer Hector, Osnabrueck (DE)

(73) Assignee: B. BRAUN AVITUM AG, Melsungen (DE)

( * ) Notice: Subject to any disclaimer, the term of this patent is extended or adjusted under 35 U.S.C. 154(b) by 10 days.

(21) Appl. No.: 14/784,463

(22) PCT Filed: Apr. 16, 2014

(86) PCT No.: PCT/EP2014/057747
§ 371 (c)(1),
(2) Date: Oct. 14, 2015

(87) PCT Pub. No.: WO2014/170380
PCT Pub. Date: Oct. 23, 2014

(65) Prior Publication Data
US 2016/0129174 A1    May 12, 2016

(30) Foreign Application Priority Data

Apr. 19, 2013  (DE) .................... 20 2013 101 695 U
Jan. 13, 2014  (DE) ........................ 10 2014 100 326

(51) Int. Cl.
A61B 19/00    (2006.01)
A61M 1/16    (2006.01)
(Continued)

(52) U.S. Cl.
CPC ............ *A61M 1/1668* (2014.02); *A61J 1/201* (2015.05); *A61J 1/2048* (2015.05); *A61J 1/22* (2013.01);
(Continued)

(58) Field of Classification Search
CPC .............. A61M 1/1668; A61M 1/3643; A61M 1/3647; A61M 1/367; A61M 39/223;
(Continued)

(56) References Cited

U.S. PATENT DOCUMENTS 5,004,548 A   4/1991  Richalley et al.
5,527,306 A   6/1996  Haining
(Continued)

FOREIGN PATENT DOCUMENTS

CN    1077654    10/1993
CN    102015015    4/2011
(Continued)

OTHER PUBLICATIONS

Chinese Office Action and Search Report, with translation, for CN 201480022314.X dated Aug. 1, 2016.
(Continued)

*Primary Examiner* — Philip R Wiest
(74) *Attorney, Agent, or Firm* — RatnerPrestia

(57) ABSTRACT

Disclosed is a filling device of a fluid conducting system of an extracorporeal blood treatment device that includes a spike for connecting to the single fluid connector of a medical fluid container and a manually operable fluid blocking mechanism arranged directly downstream of the spike that fluidly connects with the spike while the filling device is in operation. The fluid blocking mechanism has at least one fluid outlet connector that is adapted so that a line section or hose of the fluid conducting system such as the arterial line section of a blood purification device can be
(Continued)

connected to it in a detachable manner while the filling device is in operation.

6 Claims, 2 Drawing Sheets

(51) Int. Cl.
   *A61M 39/22* (2006.01)
   *A61M 1/36* (2006.01)
   *F16K 11/072* (2006.01)
   *F16K 31/60* (2006.01)
   *A61J 1/22* (2006.01)

(52) U.S. Cl.
   CPC .......... *A61M 1/367* (2013.01); *A61M 1/3643* (2013.01); *A61M 1/3647* (2014.02); *A61M 39/223* (2013.01); *F16K 11/072* (2013.01); *F16K 31/60* (2013.01)

(58) Field of Classification Search
   CPC .. A61J 1/10; A61J 1/201; A61J 1/2048; A61J 1/22; F16K 11/072; F16K 31/60
   USPC ......................................................... 604/407
   See application file for complete search history.

(56) References Cited

U.S. PATENT DOCUMENTS

| | | | |
|---|---|---|---|
| 5,901,942 | A | 5/1999 | Lopez |
| 6,032,926 | A * | 3/2000 | Fuchs ...................... A61J 1/10 251/149.1 |
| 6,682,509 | B2 | 1/2004 | Lopez |
| 8,206,375 | B2 | 6/2012 | Snow |
| 2008/0214981 | A1 | 9/2008 | Delnevo et al. |
| 2011/0106046 | A1 | 5/2011 | Hiranuma et al. |
| 2011/0257607 | A1 | 10/2011 | Whitley |
| 2016/0106970 | A1 | 4/2016 | Fangrow |

FOREIGN PATENT DOCUMENTS

| | | |
|---|---|---|
| CN | 102307604 | 1/2012 |
| CN | 102448537 | 5/2012 |
| WO | WO 97/21464 | 6/1997 |
| WO | WO2012/076386 | 6/2012 |

OTHER PUBLICATIONS

International Search Report for WO 2014/170380 dated Jul. 28, 2014.
German Search Report for DE 10 2014 100 326.8 dated Feb. 28, 2014.

* cited by examiner

FILLING DEVICE OF A FLUID SYSTEM

CROSS REFERENCE TO RELATED APPLICATIONS

This application is the U.S. national phase application of PCT International Application No. PCT/EP2014/057747 filed Apr. 16, 2014, which claims priority to German Patent Application No. DE 20 2013 101 695.0 filed Apr. 19, 2013, and German Patent Application No. DE 10 2014 100 326.8 filed Jan. 13, 2014, the contents of each application being incorporated by reference herein.

FIELD OF THE INVENTION

The invention in hand concerns the filling device of a fluid conducting system and/or liquid system, in particular an extracorporeal blood treatment device, for example a dialysis or apheresis machine.

BACKGROUND OF THE INVENTION

The hydraulic system (blood-side fluid system) of a blood treatment device, for example a dialysis machine, has to be filled with fluid, for example an NaCl solution or another sterile physiological solution, before being connected up to a patient, in such a way that air pockets in the system that would be dangerous for a patient connected up to the fluids of the system are eliminated. Furthermore, the hydraulic system can be flushed with the filled-in fluid for a certain period of time in order to filter/wash out any contaminants, dirt particles, etc. that may have deposited in the system before the system is connected up to the patient. On an extracorporeal blood treatment device, these two procedures are performed in the scope of a filling—circulation cycle.

In the state of the art, there are fluid containers preferably in the shape of plastic bags designed especially for extracorporeal blood treatment devices of this relevant type in order to enable, among others, the device functions as described above. This kind of fluid containers is also manufactured and sold by the applicant filing the application in hand.

As a rule, such a fluid container has a fluid intake chamber and two, preferably closable, fluid connectors. On a first of the two connectors, an arterial line section, and on the second connector, a venous line section of the hydraulic system (fluid system or also referred to as fluid conducting system) of the extracorporeal blood treatment device can be connected. The fluid bag as well as the two line sections together constitute a circulation device of the extracorporeal blood treatment device.

For the fluid system filling process, first the arterial line section is connected to the first fluid connector of the bag, and after opening of the first fluid connector, the hydraulic system is filled. The venous line section of the system first remains open to the atmosphere or is connected to a drain, a container or a bag so that air inside the system can escape/be vented. As soon as the filling process is completed, the venous line section is connected to the second fluid connector of the bag in order to circulate the fluid inside the hydraulic system of the extracorporeal blood treatment device for a certain period of time or a certain volume of flow through the bag chamber.

During this optional circulation process, the fluid flows through internal filtering devices of the system in which remaining air pockets are removed/filtered out with the fluid. If necessary, the venous line section of the hydraulic system can again be disconnected from the second fluid connector of the fluid bag and the fluid inside the hydraulic system can be flushed out again under constant supply of fluid from the container.

Upon termination of the optional circulation process, the filling/circulation cycle preparing for patient treatment is completed so that the two line sections (venous and arterial) can be disconnected from the fluid bag and connected up to the patient for treatment.

The description above of the filling/circulation cycle of a hydraulic system/fluid conducting system of an extracorporeal blood treatment device (dialysis machine) known from the state of the art indicates that the fluid bag remains in the system circuit for the filling and circulation processes, i.e. that the fluid inside the system is circulated through the fluid bag and/or its fluid chamber. As a result, the fluid in the fluid bag may get contaminated. The consequence of this is that with each new treatment preparation of the extracorporeal blood treatment device, a new fluid bag with fresh, uncontaminated fluid is used for the following filling/circulation cycle, whereas the fluid bag for the filling/circulation cycle performed before is disposed of independently of its residual content. It is obvious that this procedure results in the wasting of a large quantity of fluid in case of a high patient treatment number because the fluid content of a fluid bag can only be used (incompletely) for one filling/circulation cycle.

Furthermore, the fluid bags for blood treatment devices effectively concern a custom-made design with two separate fluid connectors, as a result of which manufacturing becomes more expensive due to smaller numbers as compared with conventional NaCl bags/bottles on the whole. In the end, the handling of the filling device according to the description above is not ideal. As a result, at least the arterial connector has to be connected to the fluid bag for filling the system with fluid in order to fill the system with fluid from the fluid bag and to vent it based on the "single-pass principle," with the venous connector being open to a drain, a container or bag or to the atmosphere. Then the arterial connector has to be disconnected from the fluid bag and connected to an arterial patient access.

SUMMARY OF THE INVENTION

Here, it is to be pointed out that class-specific filling devices according to the description above as well as the filling device according to aspects of the invention naturally can be provided not only for fluid conducting systems for use on extracorporeal blood treatment machines, but can also concern other fluid conducting systems such as heart-lung machines, infusion systems, etc., and therefore should be able to be used for multi-functional purposes.

In view of these problems, an object of the invention in hand is to provide a filling device of a fluid system of this kind, for example an extracorporeal blood treatment device, which can be operated more efficiently and thus more cost-efficiently as compared to the state of the art. Furthermore, a purpose of the invention in hand is to make available a fluid system equipped with the filling device according to aspects of the invention, for example an extracorporeal blood treatment device, that can be operated in a simple manner and that enables the use of conventional fluid bottles (e.g. NaCl bottles) for their multi-functional use.

This object is solved with a filling device of a fluid system/liquid system (means for filling a fluid system), preferably an extracorporeal blood treatment device (dialysis machine), a heart-lung machine, etc., with the characteristics of the independent claim. Furthermore, the further goal is achieved with a fluid conducting system (means for conducting fluid). Advantageous embodiments of the invention are the subject matter of sub-claims.

The basic idea of the invention in hand is to design the class-specific filling device of a fluid conducting system, in particular an extracorporeal blood treatment system, in such a way that a conventional (price-effective) fluid container (means for storing fluid) of a known design such as a conventional NaCl bottle or a suitable bag with only one puncturable/connectable connector can be used. Furthermore, the filling device according to aspects of the invention has, as a central component, a so-called spike (means for puncturing a fluid container), for connecting up to the single fluid connector of a conventional medical fluid container to which a fluid blocking mechanism (means for blocking a fluid flow) that at least closes automatically (and also opens, if necessary), for example a stop valve, is connected downstream, which is adapted or designed in such a way so as to remain constantly fluidically connected with the spike. The fluid blocking mechanism is designed in such a way that it closes automatically as a result of a fluid flow in spike flow direction, i.e. from the punctured fluid container to the spike connector for the fluid conducting system, and can be opened optionally with a mechanical activation mechanism (means for mechanical activity a fluid blocking mechanism to be open) against the fluid flow.

Preferably, this activation mechanism is designed in such a way that it is effectively activated automatically upon/by connecting up of the fluid conducting system to the spike/ spike connector. When the fluid conducting system is thus again disconnected from the spike, the activation mechanism releases the fluid blocking mechanism so that it is closed by the fluid that continues to flow from the fluid container for a short period of time/in a small quantity.

In order to improve the function of the fluid blocking mechanism and also to maintain it, it can be integrated in the spike and is so protected by the spike (usually made of a robust plastic material) from outside influences. Preferably, the fluid blocking mechanism is arranged in the fluid connector of the spike for the fluid conducting system and adapted in such a way that is it activated by the cooperating fluid connector of the fluid conducting system in the open position.

According to an aspect of the invention in hand, the fluid blocking mechanism, and in particular the stop valve, thus has an axially movable valve body means inserted in the spike, and preferably in the line connector of the spike, and a valve seat means acting in spike flow direction which can be closed by the valve body through the fluid flow/the fluid pressure. Furthermore, the valve body has an actuator which preferably protrudes through the valve seat and is adapted in such a way that is (mechanically) automatically activated by a line section or its connector for a (forced) opening of the stop valve when the line section is connected to the spike and/or its line connector.

In other words, the stop valve is designed in such a way that it is brought in an open position upon connection of a line section of the fluid conducting system as well as through the connecting process (mechanical) in order to allow a fluid flow from a medical fluid container punctured by the spike through the force-opened stop valve in the fluid conducting system. When the line section is uncoupled or disconnected from the spike and/or its line connector, the stop valve closes automatically (hydraulically) as a result of the (continued) flow of fluid that lasts for a short while from the medical fluid container, and is then kept in the closing position by the stagnation pressure that develops.

In order to accelerate the closing process and to keep the fluid leakage that occurs in course of it (during that) as small as possible, a pre-tensioning device means, for example a spring, helical compression spring or an elastomer or the like can be arranged in an advantageous manner, which pre-tensions the valve body in its closing position.

Here it has to be pointed out that the stop valve does not necessarily have to be a poppet valve, but can also be designed according to another aspect of the invention in hand as a sliding or rotary valve, whereby in this case the valve body is designed as a valve coil with at least two switch positions. In this case, the valve housing would have an inlet and an outlet which are connected with or disconnected from each other according to the switch position of the valve coil. This means that in the one switch position, the valve coil establishes a connection between the spike and its line connector, whereas in the other switch position, this connection is disconnected. In this case as well, the valve coil can be pre-tensioned spring-elastic in the disconnect/ and/or shut-off switch position. Such possibly spring-pretensioned, mechanically/manually or hydraulically activated 2-way/2-position switch valves are per se generally known from hydraulics so that a detailed design description is not necessary here.

The (mechanical) activation of the valve body is realised according to another aspect of the invention in hand, preferably with the connector of the line section or the line section (fluid conducting system) itself. The activation can be realised directly or with an inserted actuator which is arranged movable in the spike and in particular in the spike's own connector. In the latter case, it is possible to arrange the actuator in such a way that it can also be activated manually, with the line section uncoupled, to open the stop valve, e.g. for flushing, or to close the stop valve in case of a malfunction (valve body gets caught).

Due to the arrangement of the fluid blocking mechanism in the spike that closes automatically and also opens automatically due to the connecting process of a fluid line section to the spike, the spike can remain on the conventional medical fluid container after puncturing of the container seal, whereas the line section can optionally be connected to the fluid blocking mechanism and/or the spike for a filling process of the fluid conducting system and can afterwards be disconnected from the fluid blocking mechanism/the spike again without fluid getting lost from the medical fluid container (or only a small/negligible fluid volume getting lost). After the line section is disconnected from the outlet connector of the spike (e.g. Luer-Lock fitting), the line section can be reconnected to a patient access, for example, immediately afterwards without any changes having to be performed on the line section and/or its connector. This simplifies the handling of the filling device.

The fluid container and/or its stored liquid/fluid can furthermore be used for several subsequent treatments/ filling processes depending on its filling volume. Furthermore, the medical filling device is provided for a conventional/universal medical fluid container, which is more cost-efficient, for example, in comparison with the specially designed containers with two connectors for extracorporeal blood treatment devices.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

According to FIG. 1, an extracorporeal blood treatment device 1, for example a dialysis machine, heart-lung machine, etc., has an internal hydraulic conducting system (hereinafter referred to as fluid conducting system) through which during a treatment phase on the machine side, for example, a blood purification fluid (dialysis fluid) is passed, and on the patient side, blood flows through it extracorporeally in the opposite direction, whereby the machine-side and the patient-side fluid conducting system sections are fluidically separated in case of a dialysis machine by a dialyser (filter).

For this purpose, the fluid conducting system (system section) has a venous line section and an arterial line section 2, 4 on the blood-/patient side, preferably with connectors (e.g. Luer-Lock fittings) 6, 8 on each hose section arranged/formed on the ends in each case to which, for example, injection needles or cannulas (not depicted) can be connected as patient access, which can be introduced in a patient's body.

In order to avoid a possibly necessary washing out of possible contaminations, resulting from manufacturing, in the patient's body and to expel air enclosed in the conducting system, the extracorporeal blood treatment device 1 can be connected to a filling device with which the patient-side fluid conducting system is flushed/cleaned as a rule before every patient treatment.

Figure 1:
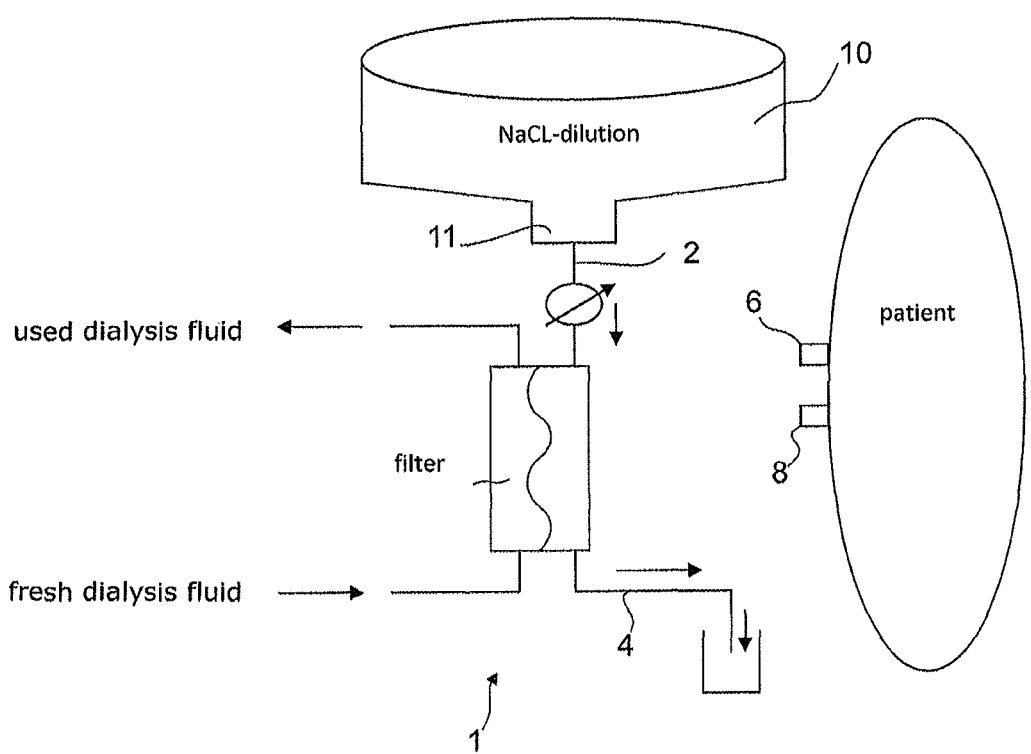
FIG. 1 conceptionally shows a fluid system of an extracorporeal blood treatment device according to a preferred exemplary embodiment of the invention, whereby the blood-side system is connected to a fluid source (fluid container) for a filling process based on the "single-pass principle.
Figure 2:
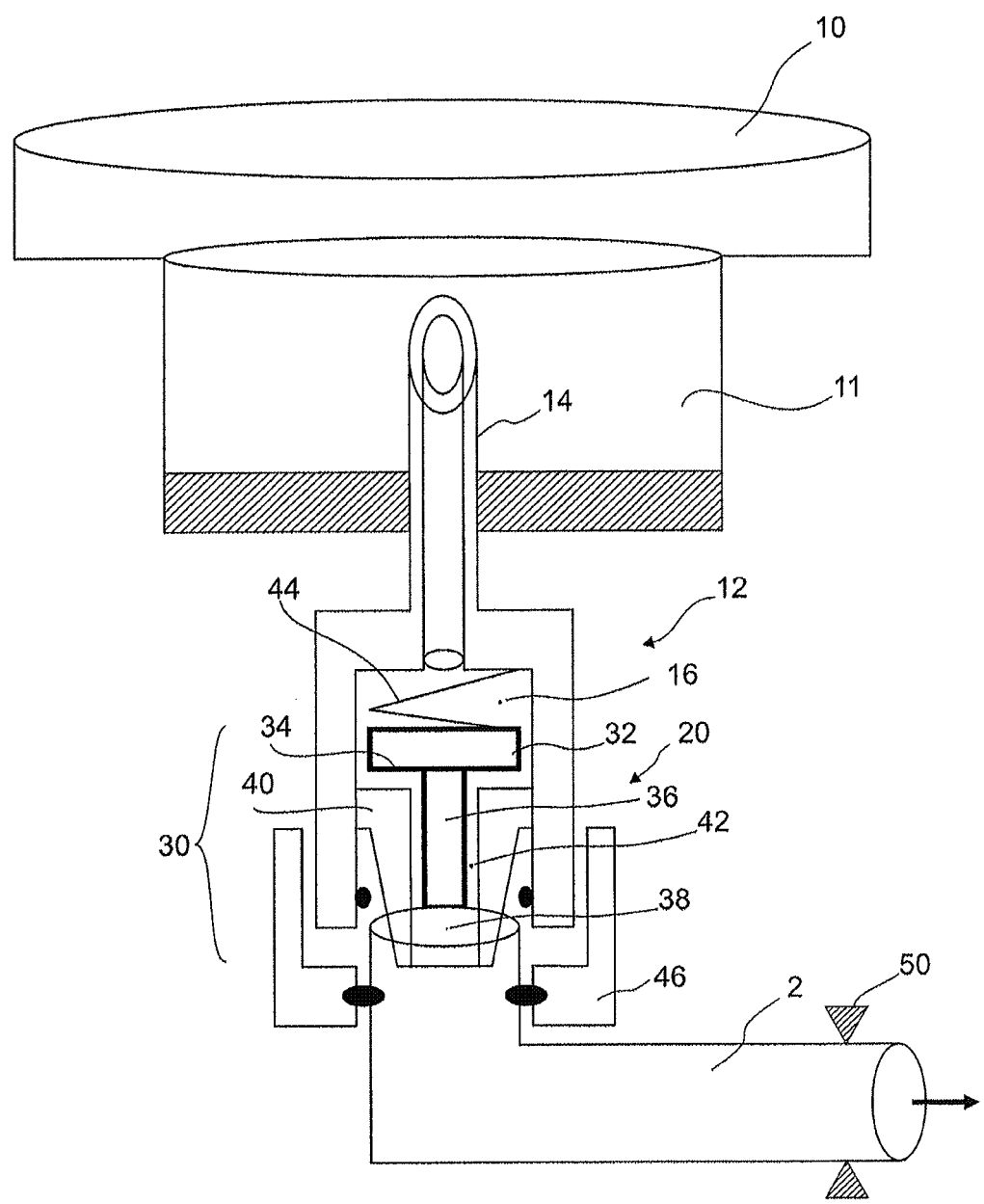
" and FIG. 2 shows a fluid blocking mechanism according to a preferred exemplary embodiment of the invention which is integrated in a spike for connector of the blood-side system section on a conventional fluid container.

According to FIG. 1, the filling device according to aspects of the invention in hand has a fluid source, preferably in the form of a universal fluid container (NaCl bottle) 10, with a single outlet 11 which is punctured in the exemplary embodiment in hand with a so-called spike 12 (see FIG. 2) of the filling device in order to tap fluid from the fluid container 10. According to FIG. 2, the spike 12 has an (outlet) connector 20, preferably in the form of a Luer-Lock fitting, to which the arterial line section 2 can be temporarily connected for a filling and/or flushing process. The spike 12 and its connector 20 for the line section 2 are conceptionally shown in FIG. 2.

Accordingly, the spike 12 has a pricking section in the form of a hollow-bore needle or cannula 14 to which the connector 20 is directly connected downstream. The connector (Luer-Lock fitting) 20 and the cannula 14 are integrated in an modular unit. As an alternative to the Luer-Lock fitting, however, it is also conceivable to design the spike connector 20 as a simple slip-on fitting onto which the line section, for example in the form of a flexible hose, can be slid. Every other connector structure of a known design is conceivable as well. Within the spike 12 and, preferably according to the exemplary embodiment in hand, within the connector 20, a reception space 16 is formed, which houses a fluid blocking mechanism 30.

Even if the fluid blocking mechanism 30 is described as an integrated part of the spike 12/spike connector 20 below, it is basically conceivable to realise the fluid blocking mechanism 30 according to the description below as a separate cartridge, which is simply inserted in the spike 12 or its connector 20 (in the receiving space 16) in order to equip/retrofit a conventional spike with the fluid blocking mechanism according to aspects of the invention, for example, in that way.

In particular, the fluid blocking mechanism 30 according to aspects of the invention has, according to the preferred exemplary embodiment of the invention, a valve body 32 with a flat, conical or spherical seat section 34, to which an actuator is connected, in this case, for example, in the form of a bar or pin 36, preferably in one piece, in axial direction of the spike 12 in the direction to the spike connector 20. Within the receiving space 16, the valve body 32 is incorporated so that is axially movable, and fluid from the fluid container 10 can flow through it or around it.

Within the receiving space 16, downstream of the valve body 32, a valve seat 40 is formed, with which the valve body 32 can be put in an abutting position with a sealing effect when it moves downstream in order to close a valve feed-through 38 in the valve seat 36. The bar-shaped actuator 36 has an outside diameter that is smaller than the diameter of the valve feed-through 38 so that the actuator 36 can project through the valve feed-through 38, thus forming an annular flow clearance 42 and can protrude from the spike connector 20. On the side of the valve body 32 turned away from the valve seat 40, preferably a pre-tensioning spring 44 is arranged, which presses the valve body 32 against the valve seat 40.

The function of the filling device with the conceptional design described above can be illustrated as follows:

When the fluid conducting system presented (blood-side conducting system of a dialysis machine) is to be filled with fluid first for a subsequent patient treatment, for example an NaCl solution, first the arterial line section is connected with the connector 20 of the spike 12 according to aspects of the invention. In case of a Luer-Lock fitting, this is realised with a kind of cap nut 46 which is screwed on the connector 20 and pushes the (hose) pipe 2 fluid-tight in the connector 20 in the process.

Upon the screwing-on of the cap nut 46 and/or the pushing-in of the line section 2 or its co-active connector (not shown) in the spike connector 20, the bar 36 is effectively also pushed automatically as a mechanical activation mechanism of the stop valve 30 against the pre-tensioning spring 44, axially in the receiving space 16, and the valve body 32 and/or its seat section 34 are lifted off the valve seat 40 in the process. In this mechanically force-opened state, fluid can now flow from the fluid container 10 through the spike 12 in the downstream (hose) conducting system 2.

When the conducting system 2 is uncoupled from the spike 12, the axially force-shifted bar 36 is released, whereupon the valve body 32 is pressed against the valve seat 40 by the fluid still flowing from the fluid container 10 and the pre-tensioning force of the spring 44 and so closes the stop valve 30. On the free end of the line section 2, there may be a hose clamp 50 which temporarily seals the conducting system after uncoupling from the spike 12 until the conducting system has been connected to the patient access.

As a result of the integration of the stop valve 20 in the spike 12, the line between the fluid container 10 to the valve seat 40 becomes very short, which improves the response characteristics of the valve. Furthermore, the housing of the spike 12 protects the movable parts of the stop valve 20 and so ensures that it remains functional. Finally the spike 12 according to aspects of the invention is a disposable item that can be produced for a reasonably price and is disposed after every use. Consequently no cost-intensive cleaning work needs to be performed on the stop valve.

The stop valve 20 described above is presented in this case as a poppet valve with valve body 32 and valve seat 40. For this purpose, the valve body does not necessarily have to be a plate, but can also have the shape of a ball, a cone, etc. Furthermore, the stop valve described can also be designed as a sliding or rotary valve of a known structure, in which instead of the valve body shown, a moving valve piston axially or radially arranged to the spike 12 is provided, which in a first, mechanically activated position, optionally connects the cannula 14 with the outlet connector of the spike 12, and in a second, mechanically non-activated position, disconnects the connection between cannula 14 and spike connector. The valve piston can also be pre-tensioned with a spring in shut-off position on one side.

Accordingly, disclosed is a filling device of a fluid conducting system, preferably an extracorporeal blood treatment device (1), which has the following components:
- a spike 12 which is adapted for connecting the single fluid connector of a medical fluid container 10 of the fluid system and
- a manually operable fluid blocking mechanism 30 which is arranged directly downstream of the spike 12, preferably integrally in the spike 12, and is adapted or provided in such a way so as to remain fluidically connected with the spike (12) while the filling device is in operation, whereby
- the fluid blocking mechanism 30 has at least one fluid outlet connector which is adapted so that a line section/hose 2 of the fluid conducting system, preferably the arterial line section of the blood purification device, can be connected to it in a detachable manner while the filling device is in operation.

The invention claimed is:

1. Filling device of a fluid conducting system of a medical treatment device, comprising:
   a spike adapted for connecting a fluid connector of a medical fluid container to the fluid conducting system, the spike having a pricking cannula on which there is a spike outlet connector with a receiving space downstream of the pricking cannula, the spike outlet connector configured such that a line section or hose of the fluid conducting system can be connected in a detachable manner while the filling device is in operation;
   a manually operable fluid blocking mechanism positioned downstream of the pricking cannula in the receiving space, the fluid blocking mechanism fluidly connected with the spike while the filling device is in operation, wherein:
   the fluid blocking mechanism is installed in the receiving space to form an integral unit with the spike such that the fluid blocking mechanism is mechanically activated in an open position upon or through connection of the line section or hose of the fluid conducting system to the spike against fluid flow in the spike; and
   the fluid blocking mechanism is a manually operable poppet valve having a valve body axially mounted in the receiving space that interacts with a valve seat in the receiving space; and
   a pre-tensioning spring arranged on a side of the valve body facing away from the valve seat to press the valve body against the valve seat.

2. Filling device according to claim 1, further comprising an activation mechanism for the mechanical activation of the fluid blocking mechanism through the connection process of the line section or hose of the fluid conducting system to the spike.

3. Filling device according to claim 2, wherein the activation mechanism is a bar or pin formed on the valve body that is activated into the open position by the line section or hose of the fluid conducting system upon its connection to the spike by an axial movement.

4. Filling device according to claim 1, wherein the fluid blocking mechanism is a separate valve cartridge which houses all valve components and which is adapted for insertion in the receiving space of the spike.

5. Use of a filling device according to claim 1 for filling a blood-side fluid conducting system of a dialysis machine with an NaCl solution.

6. Procedure for filling a blood-side fluid conducting system of a dialysis machine with an NaCl solution, wherein the procedure provides for the use of a filling device according to claim 1, wherein:
   a. first an arterial line section is connected to the fluid outlet connector of the spike for a flushing process of a downstream hose pipe system of the dialysis machine, and
   b. the arterial line section is uncoupled from the connector as final preparation for a subsequent connection of the hose pipe system to a patient.

\* \* \* \* \*